United States Patent [19]

Elsohly et al.

[11] 4,428,965

[45] Jan. 31, 1984

[54] TOLERIZING AND DESENSITIZING COMPOUNDS, COMPOSITIONS AND METHODS OF TREATMENT AGAINST DERMATOLOGICAL CONDITIONS CAUSED BY ALLERGENS FROM PLANTS AND TREES OF THE ANACARDIACEAE AND GINKGOACEAE FAMILIES

[75] Inventors: Mahmoud Elsohly; Edna S. Watson; Coy W. Waller, all of Oxford, Miss.

[73] Assignee: The University of Mississippi, University, Miss.

[21] Appl. No.: 44,351

[22] Filed: May 31, 1979

[51] Int. Cl.³ .................. A61K 31/22; C07C 69/00
[52] U.S. Cl. .................. 424/311; 424/101; 560/144
[58] Field of Search ............ 424/311, 101; 560/144

[56] References Cited

U.S. PATENT DOCUMENTS 2,833,825  5/1958  Lewis ............................ 560/144 X
3,294,836 12/1966  Peterson et al. ............... 560/144 X
3,624,135 11/1971  Kablaoui ......................... 560/144
3,631,227 12/1971  Kablaoui et al. ............... 560/144

OTHER PUBLICATIONS

The Merk Index–9th Ed., p. 9553, (1976).
Hill et al., J. Am. Chem. Soc. 56: 2736 (1934).
Srinivasan et al., Analytical Biochemistry, 6: 234 (1963).

Primary Examiner—Leonard Schenkman
Attorney, Agent, or Firm—William D. Stokes

[57] ABSTRACT

Compounds, compositions and a method of treatment to tolerize and desensitize mammals sensitive to the allergenic moities found in plants of the Anacardiaceae and Ginkgoaceae families comprising the reaction product of poison ivy urushiol, poison oak urushiol, poison sumac urushiol & mixtures thereof, 3-n-alkane substituted catechol derivatives having 11 to 19 carbon atoms and the unsaturated olefinic congeners thereof with an acyl ester functioning group esterifying the catecholic hydroxy constituents of the aforementioned compounds or cell membrane residues.

68 Claims, No Drawings

TOLERIZING AND DESENSITIZING COMPOUNDS, COMPOSITIONS AND METHODS OF TREATMENT AGAINST DERMATOLOGICAL CONDITIONS CAUSED BY ALLERGENS FROM PLANTS AND TREES OF THE ANACARDIACEAE AND GINKGOACEAE FAMILIES

SUMMARY OF THE INVENTION

This invention is concerned with compounds, compositions and methods of treatment for developing tolerance, desensitization or hyposensitization to poison ivy, poison oak, poison sumac and raw cashew nuts as well as other dermatogenic plant species. More specifically, the invention is directed to new compounds and conjugates and compositions thereof and a method of treatment for tolerization, desensitization or hyposensitization of mammals susceptable to sensitization to the allergenic components of *Toxicodendron radicans* (poison ivy); *Toxicodendron diversilobum* (western poison oak); *Toxicodendron quercifolium* (eastern poison oak); *Toxicodendron vernix* (poison sumac); *Anacardium occidentale* (cashew nut shell oil) and other dermatogenic plant species, e.g., *Rhus striata* (Manzanillo); *Rhus verniciflua* (Japanese Lac); *Mangifera indica* (mango); *Semicarpus anacardum* (India ink tree); and *Ginkgo biloba L.* (Ginkgo tree). Specifically, the invention comprises new compounds comprising urushiol catechol moieties having the formula

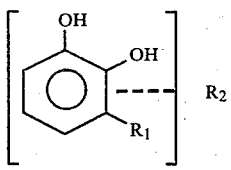

wherein $R_1$ is an alkane having 11 to 19 carbon atoms or an unsaturated congener thereof, and $R_2$ is an acylester function substituted on the phenolic hydroxy groups of the catechol, or cell membrane residues conjugated with the urushiol catechol. The invention further includes desensitizing and tolergenic compositions comprising one or a mixture of said compounds in admixture with a non-toxic, pharmaceutically acceptable carrier. The invention additionally includes a method for tolerizing, desensitizing and/or hyposensitizing mammals to the allergenic effects of poison ivy, poison oak, poison sumac, cashew nut shell oil and other dermatogenic plants. The compounds and compositions of the invention can be given in effective, non-toxic doses and are effectively administered in admixture with the known non-toxic, pharmaceutically acceptable diluent carriers.

BACKGROUND OF THE INVENTION

It is estimated that over 1.5 million cases of poison ivy are encountered every year with a concomittant loss of over 152,000 work days in the United States. There are no successful treatments known in the art for developing tolerance in, or desensitization of sensitive mammals to poison ivy or the related allergenic causing plants of the Anacardiaceae family.

The methods employed to attempt treatment or prevention of dermatitis caused particularly by contact with poison ivy, poison oak and poison sumac have, historically, followed three avenues of approach namely, antigens, topical agents, and chemical barriers. For brevity in this discussion, the term allergenic agent is to be understood to include the allergenic agents contained in poison ivy, poison oak, poison sumac and cashew nut shell oil, which are the principal dermatitis causing plants and substances of the family Anacardiaceae found all over the world. Of these plants, poison ivy, per se, is the most widely distributed species in the United States. There are many species of poison ivy in North America. The various species are distinguished primarily according to leaf shape. The varying leaf shapes led to considerable confusion among botanists in view of the fact that the leaf shape of a given species also can vary according to geographical location and even on the same plant of any species.

Antigen treatment of poison ivy is said to have been practiced by the American Indian (Gilmore, M. R., in the 33rd Annual Report, 1911–1912, Bureau of American Ethmology, Washington, D.C., Smithsonian Institution, p. 43, 1912). The methods said to have been employed by the American Indian were revived and popularized in the early part of the century (Schamberg, J. F., "Desensitization of Persons Against Ivy Poison". *J.A.M.A.*, 73:1213, 1919). Numerous topical treatments using various chemical compounds and compositions have been proposed and used. Exemplary of such topical treatments include various oxidizing agents, for example, sodium perborate and zinc oxide. The topical treatments proposed and used over the years are intended to destroy the allergenic principle before penetrating the skin (Shelmire, B., "Sodium Perborate Ointment and Poison Ivy Dermatitis". *J.A.M.A.*, 116(8): 681–683, 1941). Unfortunately, none of the known topically applied agents have been successful, moreover, in many cases, such agents have aggravated the dermatological condition caused by the allergens, even to the extent of spreading of initially localized erythemic and edemic reactions to other areas of the body. Reagents which are designed to act as barriers to allergens contacting the skin have also been proposed. Among such "barrier" agents are ionic exchange resins (Thurman, Francis M., Bertha Ottenstein, and Maurice J. Bessman, "Chemical and biological tests with the toxic substance of poison ivy (urushiol) and its absorption by amberlite ion exchange resins" *Journal of Investigative Dermatology*, 25:9–20, 1955). Unfortunately, as in the case of the variously proposed topical agents, none of the barrier chemicals have offered any degree of success. There are many known and proposed anti-pruritic agents such as calamine lotion, petrolation and steroids for use to relieve itching and inflammation. None of the known topically applied compounds or compositions have been successful in either treatment or prevention of poison ivy, poison oak, poison sumac or cashew nut shell extract caused dermatitis.

The medical profession, for many years, used treatments comprising injections of Rhus preparations (namely: ivy, oak and sumac) into humans and animals which allegedly created antibodies to the allergenic agents. Supportive evidence of the therapeutic usefulness for such treatments was based on favorable reports by clinicians in, for example, Schamberg, J. F., "in discussion on papers of Hermann, Knowles, and White." *J.A.M.A.*, 68:87, 1917.

Schamberg, J. F., "Desensitization of persons against poison ivy." *J.A.M.A.*, 73:1213, 1919.

Schamberg, J. F., "Poison ivy treatment." *Archives of Dermat. & Syph.*, 11:266, 1925.

Alderson, H. E., "Treatment of Poison Ivy Dermatitis." *California and West. Med.,* 23:282, 1925.

Alderson, H. E. and Pruette, H. J., "Poison Oak Dermatitis (A specific treatment): Fatal results among Indians and Mexicans from eating leaves of Poison Oak plant." *California State J. Med.,* 19:188, 1921.

Bivings, F. L., "Successful desensitization and treatment of poison ivy and poison oak poisoning." *Arch. Dermat. & Syph.,* 9:602, 1924.

Williams, C. M., *M.J. & Rec. (supp.),* 119:131, 1924.

Williams, C. M. and MacGregor, J. A., "Treatment of ivy poison by Rhus Tincture and antigen." *Arch. Dermat. & Syph.,* 10:515, 1924.

This sanction of the use of poison ivy extracts was followed by widespread use of preparations for poison ivy hyposensitization, desensitization and treatment. Unfortunately, the clinical data supporting such treatments was found to be, for the most part, misleading and unreliable. The use of extracts created numerous problems and in quite a few reported instances dangerous pathological conditions. The medical profession now strongly denounces treatment of acute poison ivy dermatitis with such preparations. At their best, the treatment is cumbersome, time consuming, the results unpredictable, and the treatment is fraught with discomfort and danger to the patient. In the relatively few cases where desensitization has occurred, large dosage units of the toxic compound have been required over months and years and sensitivity is rapidly regained on cessation of treatment.

It is known that the dermatogenic principles contained in the resin of poison ivy, poison oak and poison sumac are a group of chemically related catechols, commonly referred to as urushiols, differing mainly in the length and degree of unsaturation of the 3-n-alkyl side chain. Poison ivy urushiol has been shown to be mainly ($>95\%$) a mixture of 3-n-pentadec-(en)-ylcatechols with 0,1,2, and 3 double bonds in the $C_{15}$ side chain. Poison oak urushiol, however, consists mainly ($>98\%$) of the $C_{17}$ homologues. A small percentage of the $C_{15}$ congeners were found in poison oak urushiol and of the $C_{17}$ homologues in poison ivy components. The analysis and identification of poison sumac urushiol is incomplete. While it has been reported that poison sumac urushiol is principally a mixture of 3-n-pentadec-(en)-ylcatechols similar to that of poison ivy, poison sumac analyzed by the inventors was shown to consist entirely of the $C_{15}$ catechols with a previously undescribed principal component ($>60\%$ of total urushiol) having 3 double bonds in positions different from those in the triolefinic component of poison ivy urushiol. This new component of poison sumac urushiol will hereafter be referred to as poison sumac urushiol (PSU). Cashew nut shell extract principally comprises the three compounds, anacardic acid, anacardol and cardol with varying degrees of unsaturation in the $C_{15}$ side chains.

The total urushiol concentration and the relative proportion of the individual congeners may vary according to plant part, age of plant, season and place of collection. Notwithstanding, it is a well-known fact that contacting the skin of susceptible individuals or animals with any one of these plants or their constituents results in sensitization to all the allergenic compounds of the family Anacardiaceae. Heretofore, once sensitivity to any of the allergens was developed it was difficult, if not impossible, to eliminate.

DESCRIPTION OF THE PREFERRED EMBODIMENTS

The animals used in the tests of the invention were female Camm-Hartley line-bred guinea pigs weighing 450-500 grams. All animals were acclimatized for a minimum of one week prior to use and ear tatooed for permanent identification. The animals were weighed at the beginning of the tests and at two week intervals thereafter. All animals were identically housed and fed.

3-n-pentadecylcatechol, 3-n-heptadecylcatechol and their respective unsaturated congeners, poison sumac urushiol and cashew nut shell oil used in the examples hereinafter and in the preparation of the new compounds of the invention were prepared from purified poison ivy, poison oak, poison sumac and raw cashew nut shell extracts. The catechol urushiol compounds used were purified by repeated chromatography. The identity and purity of the compounds and their respective congeners was determined by gas chromatography and GC/MS. Synthetically prepared 3-n-pentadecylcatechol, 3-n-heptadecylcatechol, and 3-n-nonadecylcatechol were also used in the testing of the invention. The methods used to prepare the respective compounds are discussed hereinafter with reference to specific examples. The method of preparing individual congeners used in the tests is discussed also in specific examples described hereinafter. In the preferred embodiments of the invention, the $R_1$ side chain contains 15-19 carbon atoms.

We have found that animals treated with the compounds and compositions of the invention in accordance with the method of the invention were either completely protected or hyposensitized to the sensitizer compounds for remarkably extended periods of time, and perhaps, even for life. While the specifically detailed examples of the invention hereinafter describe the compositions comprising allergen-red blood cell conjugates, or allergen-acetate esters, other acylester functioning compounds and conjugated compounds of this invention may be successfully prepared using, for example, lymphatic cells, white blood cells, spleen cells, lymph node cells, butyrates, succinates, and esters of amino acids. In addition, other esters which can be hydrolyzed, in vivo, can be used for production of tolerance, desensitization or hyposensitization.

Treatment is preferably by intravenous administration in a pharmaceutically-acceptable carrier. Examples of acceptable carriers include, but are not limited to, physiological saline and a tween 60-physiological saline mixture. Successful dosage is also accomplished by oral administration of the compound in a pharmaceutically-acceptable carrier, which may be solid or liquid. Examples of acceptable solid carriers include, but are not limited to, starch, dextrose, sucrose, lactose, gelatin, agar, stearic acid, magnesium stearate, and accacia. Examples of liquid carriers include, water, and edible oils such as corn and peanut oils. When administered in solid form, the compound and diluent carrier may be in the form of tablets, capsules, powders or others prepared by standard techniques. When given as a liquid preparation, the mixture of active compound and liquid diluent carrier may be in the form of a liquid suspension administered as such or encapsulated. The compound is administered in a non-toxic, dosage concentration sufficient to induce tolerance or desensitization to allergenic effects of poison ivy, poison oak, poison sumac or cashew nut shell extract as well as other dermatogenic plant constituents of similar chemical composition. The actual dosage administered will, of course, be determined by recognized factors as age and body weight of the individual, the idiosyncrasies of the particular patient, the activity of the specific compound employed and whether or not it is a naive individual to be treated or one with developed sensitivity. Taking into consideration these varying factors from individual to individual or from mammal to mammal, the tolerizing or desensitizing dosage can be readily determined by the medical practitioner in accordance with conventional techniques in the medicinal art.

The mechanism by which tolerance, desensitization or hyposensitization is produced by the compounds, compositions and methods of the invention is not known. We have theorized, however, that the compounds of the invention bring about a release, or mechanism, whereby the allergen bind in vivo or in vitro to cell membranes and effectively blocks any opportunity of the allergens which bind to proteins of the skin to produce dermatitis. In this manner the extraordinary tolerance, desensitization or hyposensitization is accomplished by the invention.

For brevity and simplicity, abbreviations are used hereinafter in the application to describe specific chemicals and substances as follows:

| | |
|---|---|
| PDC | 3-n-pentadecylcatechol |
| HDC | 3-n-heptadecylcatechol |
| NDC | 3-n-nonadecylcatechol |
| RBC | autologous red blood cells |
| PIU | poison ivy urushiol |
| POU | poison oak urushiol |
| PSU | poison sumac urushiol |
| CNSO | cashew nut shell oil extract |
| PDC-RBC | 3-n-pentadecylcatechol red blood cell conjugate |
| HDC-RBC | 3-n-heptadecylcatechol red blood cell conjugate |
| PIU-RBC | poison ivy urushiol red blood cell conjugate |
| POU-RBC | poison oak urushiol red blood cell conjugate |
| PIU-AC | poison ivy urushiol acetate |
| POU-AC | poison oak urushiol acetate |
| PDC-AC | 3-n-pentadecylcatechol diacetate |
| NDC-AC | 3-n-nonadecylcatechol diacetate |
| CNSO-AC | cashew nut shell oil acetate. |

EXAMPLE 1

A. PDC was prepared from purified PIU by catalytic hydrogenation. The resulting PDC was purified by repeated chromatography. The identity and purity of PDC was determined by GLC and GC/MS and found to be 72% pure PDC. The purity of PDC was taken in consideration when preparing all solutions.

B. Compositions containing the urushiol compound used for sensitization were prepared in acetone at a concentration of 1 mg urushiol compound/0.15 ml acetone.

C. The compositions used for skin testing of each urushiol compound were prepared in acetone having concentrations of 3, 1, and 0.3 $\mu$g/5 $\mu$l acetone.

D. The cell membrane conjugates were prepared as follows: solutions of the urushiol compound used for RBC conjugation were prepared in propylene glycol at a concentration of 2 mg urushiol compound/ml propylene glycol. The RBC conjugate compounds of this example were prepared under aseptic conditions as follows:

1. Three ml of blood were withdrawn from each guinea pig by cardiac puncture into a heparinized syringe. Ether anesthesia was used during blood withdrawal.
2. Each blood sample was transferred to a 15 ml centrifuge tube and 10 ml of sterile physiologic saline (Travenol) was added and the cells suspended by inversion.
3. The blood suspensions were centrifuged at 2000 rpm for 10 minutes to remove the serum protein from the blood cells.
4. The supernatants were aspirated and the blood cells were resuspended with a Pasteur pipette after addition of 10 ml of saline.
5. The cells were centrifuged and the supernatant was aspirated.
6. This process of washing the blood cells with saline (steps 4 and 5) was repeated once more.
7. The blood cells were resuspended by adding 2 ml of saline to the cell pellet.
8. Each cell suspension was transferred to a 50 ml centrifuge tube containing 40 ml of saline.
9. One mg of the urushiol compound in 0.5 ml of propylene glycol was added dropwise to each cell suspension.
10. The cell suspensions were incubated for 1 hour at 37° C., centrifuged and the supernatants were aspirated and discarded.
11. The cell pellets were resuspended in 3 ml of saline and each suspension was transferred to a 15 ml centrifuge tube containing 10 ml of saline.
12. The tubes were centrifuged, the supernatants discarded, and the cells were washed twice by resuspending the cell in 10 ml saline followed by centrifugation and withdrawal of supernatants.
13. The cell pellets were then resuspended to the original 3 ml volume with saline.

The procedure for preparation of the control or sham-RBC conjugates was identical to the above-described procedure used to prepare the urushiol compound-RBC conjugate of the invention except that the propylene glycol used in step 9 did not contain the urushiol compound.

Forty-eight native guinea pigs were divided into an experimental group and a control group of 24 animals each. In this example PDC-RBC was tested for tolerogenicity for poison ivy toxins. Each RBC cell conjugate was injected intravenously into its respective guinea pig. The animals were anesthetized with ketamine (50 mg/kg) and chlorpromazine (0.5 mg/kg) intramuscularly prior to PDC-RBC injection to facilitate manipulation of the injections. The experimental group was injected with PDC-RBC two weeks prior to attempted sensitization with PDC. The control group was treated exactly as the experimental group except that the autologous red blood cells used were not conjugated with PDC.

Two weeks after injection of the experimental group with PDC-RBC and of the control group with sham-RBC all animals were given sensitizing doses of PDC as follows: 1 mg of PDC contained in 0.15 ml of acetone was applied to approximately $3cm^2$ of skin on the back of the neck which had been freed of hair. This dosage of PDC had been found to sensitize all of the animals to poison ivy urushiols. A second sensitizing attempt with PDC was made 20 weeks after the first sensitizing dose.

All guinea pigs received skin tests on the abdominal skin 14 days after the sensitizing dose and at 2-week intervals thereafter until five skin test periods had elapsed. Each animal was tested with three concentrations of PDC (3, 1, and 0.3 µg PDC/5 µl acetone) and with 5 µl acetone at each skin test period. The test solutions were dropped onto the abdominal skin from a 5 µl Hamilton syringe. Each of the four test sites was delineated with a non-toxic marker prior to application of the test solutions. The test sites were scored for presence of erythema and edema at 24, 48, and 72 hours after application of the test solutions. The Draize system of visual testing was used to evaluate the results of the tests as follows:

A. No erythema
   Erythema and eschar formation:
   Very slight erythema (barely perceptible)
   Well defined erythema
   Moderate to severe erythema
   Severe erythema (beet redness) to slight eschar formation (injury in depth)
B. No edema
   Very slight edema (barely perceptible)
   Slight edema (edges of area well defined by definite raising)
   Moderate edema (area raised approximately 1 mm)
   Severe edema (raised more than 1 mm and extending beyond area of exposure)

Animals given tolerizing dosages of PDC-RBC were remarkably protected against sensitization to PDC. None of the control group of animals were tolerized or protected in any way from sensitization by the sham treatment.

By the third test period 79% of the experimental animals developed 100% tolerance to PDC. The majority of the remaining 21% were also partially tolerant in that they did not respond to test doses of less than 3 µg PDC. The results of the tests clearly revealed that the animals treated with the conjugate of the invention developed tolerance which was profound and lasted for the entire period of the study (6 months). The tolerance developed by the animals after a single dosage of the inventive compound could not be broken by a second treatment with the allergen. Moreover, the tolerance to poison ivy produced by PDC-RBC treatment was specific in that the animals retained their ability to respond to the unrelated sensitizer DNCB. Of additional great importance, is the fact that the conjugate of the invention was completely non-toxic to the animals treated.

EXAMPLE 2

PDC prepared in accordance with the method described hereinbefore from poison ivy plants was further purified to form 100% pure PDC. The 100% pure PDC was used in the testing of this example. The purpose of this test was to rule out any conjecture that impurities in the plant extract used in Example 1 were responsible for the tolerogenic activity of the invention composition. The purification was carried out by column chromatography using dry packed silica gel 60 and chloroform as the solvent. Fractions were collected and tested for PDC using 1% alcoholic $FeCl_3$. Fractions containing PDC were pooled together, evaporated and the resulting residue was rechromatographed on MN-polyamid SC-6 (particle size <0.07 mm) column using 90% ethanol-water and the fractions containing PDC were collected, combined, and evaporated. The residue obtained was then crystallized from hexane to give colorless needle crystals of PDC, m.p. 43°. The identity of PDC was determined by GLC and GC/MS analysis.

Twenty-one female guinea pigs were acclimatized, identified and maintained as described in Example 1. Thirteen of the pigs used as the treatment group were pretreated with PDC-RBC and the remainder of the animals sham treated also as in Example 1. Two weeks following this treatment, sensitization of all pigs was attempted. Two weeks thereafter skin testing was begun and the animals were skin tested every two weeks until four skin tests had been performed on each animal. The procedures for sensitization, skin testing and evaluation of skin sensitivity were identical to those used in the testing of Example 1.

The tests of this Example conclusively revealed inter alia, that the tolerance to PDC induced by injection of the inventive PDC-RBC was reproducible and that the tolerance developed was not due to any other plant constituents than PDC. The results in this Example closely approximated the results obtained in Example 1 except that 84% of the test animals developed a substantially 100% tolerance to the PDC. All of the control animals were severely sensitive to the PDC.

EXAMPLES 3, 4 and 5

The mono-, di-, and tri-olefinic congeners of poison ivy urushiol were prepared from the purified poison ivy urushiol (72%) prepared in accordance with the method described hereinbefore.

To prepare the respective congeners, purified poison ivy urushiol (72%) was converted to its acetate derivative using acetic anhydride and pyridine. Urushiol acetate was then chromatographed on silica gel G impregnated with 5% $AgNO_3$ using 1% methanol in chloroform as the solvent system. Fractions were collected and pooled together based on their TLC similarities on $AgNO_3$ impregnated silica gel plates. The polarity of the eluting solvent was increased gradually to 4% methanol in chloroform.

Fractions were collected which corresponded to the acetates of the mono-, di-, and tri-olefinic components of poison ivy urushiol. Each fraction was then converted back to the corresponding allergenically active congener by hydrolysis of the acetates using aqueous sodium carbonate solution in dioxane-water mixture (4:1). After neutralization of the reaction mixture the free catechols were extracted with ether and the solvent evaporated. The identity and purity of the different congeners was carried out by GC and GC/MS analysis of the trimethylsilyl derivatives.

Skin testing solutions of each congener were prepared containing 3 µg/5 µl of the congener in acetone. PDC solutions viz. sensitizing solutions (1 mg PDC/0.15 ml in acetone), skin testing solutions (3, 1, 0.3 µg PDC/5 µl acetone), and tolerizing solutions (2 mg PDC/ml propylene glycol) were prepared as in Example 1 using 100% pure PDC. The treatment of the animals with the PDC-RBC conjugate of the invention was carried out as in Examples 1 and 2 using 13 guinea pigs in the experimental group and 8 animals in the control group.

The results of the tests showed that the PDC-RBC conjugate of the invention conveyed tolerance to the poison ivy urushiol congeners as well as to PDC. It was further found as a result of these tests that the severity of the erythema and edema responses in the animals increases as the degree of unsaturation in the side chain increases. In other words, the tri-olefinic component is more allergenically active than the di-olefinic congener and so on. The treated animals in these Examples followed substantially the pattern of tolerance developed in the animals of the preceding examples, i.e. 85% developed a 100% tolerance. The examples further proved that animals tolerant to PDC were also tolerant to all poison ivy urushiol congeners, that the inventive PDC-RBC conjugates convey a cross-tolerance to PDC congeners.

EXAMPLES 6, 7 AND 8

Naturally occurring poison ivy urushiol comprises about 4% of the $C_{17}$ urushiol component of poison oak while the poison oak urushiol comprises about 2% of the $C_{15}$ urushiol component of poison ivy. For use in these examples a highly purified PDC and HDC were synthesized. The PDC was prepared by reacting 2,3-dimethyoxybenzaldehyde with the Grignard reagent tetradecylmagnesium bromide in ether to produce the hydroxy derivative. Dehydration of the hydroxy derivative was accomplished by refluxing a benzene solution in the presence of a catalytic amount of p-toluenesulfonic acid, to yield 2,3-dimethoxy-3-pentadec(en)ylveratrole. Catalytic reduction of the mixture with $H_2Pd$-Cat yielded 3-pentadecylveratrole. Demethylation of this component was carried out using pyridine and HCl gas to give PDC. The PDC so produced was partitioned between ether and water. The ether extract was washed with water, $NaHCO_3$, water, and then dried over anhydrous $Na_2SO_4$ and evaporated. Pure PDC was then isolated by repeated chromatography on silica gel columns.

Pure HDC was prepared utilizing the same procedure as described above for the synthesis of PDC except that the starting materials were 2,3-dimethoxybenzaldehyde and hexadecylmagnesium bromide.

Skin testing solutions of PDC and HDC were prepared to contain 3, 1, or 0.3 μg of PDC or HDC in 5 μl of acetone. Three separate sensitizing solutions were prepared. One of the solutions contained 1 mg of PDC, one contained 1 mg of HDC and one contained 0.5 mg of each PDC and HDC each dissolved in 0.15 ml acetone. The tolerizing solutions contained 2 mg/ml of either PDC, HDC or 2 mg of a mixture of PDC and HDC (1:1) in 1 ml propylene glycol.

For these tests, thirty-six female guinea pigs were acclimatized, identified, and maintained as described in connection with Example 1. Three groups of 12 guinea pigs each were used in each test. Six animals in each group received either PDC-RBC, HDC-RBC, or PDC/HDC-RBC tolerizing treatment prior to attempted sensitization with 1 mg mixture of PDC and HDC. The remaining six animals in each group were sham treated and then one group was sensitized with PDC, another with HDC and the third with PDC-HDC mixture. At two weeks and four weeks after attempted sensitization, each respective group of animals were skin tested with 3, 1, 0.3 μg each of PDC and HDC (6 test patches on each animal). The responses of the animals to the skin test solutions were evaluated at 24, 48, and 72 hours after each skin test using the same criteria as described in Example 1. The PDC-RBC treated animals developed a high degree of tolerance to PDC and only slighter degree of tolerance to HDC, however, the HDC-RBC treated animals developed a high degree of tolerance to PDC and a moderate degree of tolerance to HDC. The PDC/HDC-RBC treated animals were also highly tolerant to both PDC and HDC sensitization. The HDC-RBC treated animals were 100% tolerant to PDC. The animals also showed either complete tolerance or greatly suppressed sensitivity to HDC (a developed hyposensitization). One of the most important and unexpected discoveries was that tolerance to both PDC and HDC developed more rapidly and to the highest degree in the animals treated with the PDC/HDC-RBC conjugate mixture.

EXAMPLE 9

Purified poison ivy urushiol (61.5%) obtained from poison ivy extract was converted to urushiol acetate by reaction with acetic anhydride and pyridine. The compound was prepared by stirring the reaction products overnight at room temperature. The reaction products were then poured over crushed ice and the mixture extracted with chloroform. The chloroform extract was washed with dilute sulfuric acid solution followed by successive washings with water and a dilute solution of sodium bicarbonate. Drying of the chloroform layer followed by evaporation of the solvent resulted in the formation of poison ivy urushiol acetate in 100% yield. The absence of any unreacted material was proven by thin layer chromatography as well as gas chromatography. Aliquots of the acetylation product were then taken which corresponded to specific amounts of urushiol. One aliquot portion of the poison ivy urushiol acetate corresponding to 100 mg urushiol was mixed in a mortar with 6 drops Arlacel (ICI, United States Inc., Wilmington, Del. 19897). To this mixture six drops of Tween 60 (Atlas Chemical Industries, Inc., Wilmington, Del. 19897) were added and trituration continued. Water was added slowly to the mixture with continuous trituration. The homogeneous emulsion was then quantitatively transferred to a 5 ml volumetric flask and the solution was diluted with distilled water to form a solution containing the urushiol acetate equivalent to 20 mg/ml of urushiol. A poison ivy urushiol acetate solution containing the equivalent of 2 mg/ml of urushiol was prepared by making a 1:10 dilution of the 20 mg/ml solution. The carrier was prepared by trituration of six drops each of Arlacel and Tween 60 with water to form 5 ml solution.

Poison sumac collected from the southern part of the state of Mississippi was differentiated into leaflets, petioles, stems and bark. Each part was separately extracted and analyzed for urushiol content and composition following the GLC procedure of the trimethylsilyl derivative (TMS) of PSU. Trimethylsilylether was prepared in accordance with the method of J. C. Craig, et al, *J. Pharm. Sci.* 67, 483 (1978). Even though occurring in varying quantities and concentrations, all of the plant parts contained urushiols. Four peaks (RRT 0.35, 0.38, 0.42 and 0.46) were identical to those found in poison ivy urushiol; a fifth strong peak (over 60% of the total, RRT 0.62) was different from any of the poison ivy urushiol components. Analysis identified the four peaks as the saturated, mono-, di- and tri-olefinic components of poison ivy. The peak with RRT 0.62 was determined to have a molecular weight of 458 and analyzed to be the TMS derivative of 3-pentadecatrienyl catechol. The position of the double bonds in this congener was not determined.

Poison sumac urushiol was prepared by ethanol extraction of poison sumac stems with subsequent partitioning between 90% methanol in water and hexane. The hexane layer containing the urushiol was purified by repeated chromatography and the new component was isolated in pure form. Since the other four components have already been tested (Examples 1 and 2), only the new component was tested in this example hereinafter referred to as PSU. PSU skin test solution was prepared in acetone to contain 3 μg/5 μl.

Eighteen female guinea pigs acclimatized identified, and maintained as in the previous examples were used in this test. The animals were assigned to one of three groups of six each. One group was given an intravenous injection of poison ivy urushiol acetate equivalent to 1 mg of urushiol A second test group was given an equivalent of 10 mg of poison ivy urushiol in the acetate form. A third group (control) was injected with the pharmaceutical carrier (0.5 ml) without the poison ivy urushiol acetate.

Two weeks following treatment, all animals were given 1 mg doses of PDC on the back of the neck in an attempt to sensitize them. Two weeks after the attempted sensitization all pigs were skin tested with 3, 1, and 0.3 μg doses each of PDC and HDC in 5 μl of the acetone carrier. The skin test sites were evaluated according to the criteria listed in connection with Example I at 24, 48, and 72 hours after each skin test. Skin tests were repeated at four, six and eight weeks after the attempted sensitization. In addition to these skin tests, both of the animal groups, treated and control, were skin tested with 3 μg of poison sumac urushiol at the sixth and eighth week. The results of the test revealed that all control animals were extremely hypersensitive to PDC, HDC and poison sumac urushiol at every skin test.

All animals treated with any dosage unit of poison ivy urushiol acetate produced 100% tolerance to PDC and poison sumac urushiol, and either tolerance or a high degree of hyposensitization to HDC. Surprisingly the 1 mg dosage unit of the inventive compound appeared to afford as great protection as the 10 mg dosage unit. Treated animals were 100% tolerant to both poison ivy and poison sumac for the two month period of the study. Complete tolerance to HDC was slower in development but throughout the test a high degree of hyposensitization to HDC was observed.

EXAMPLES 10 AND 11

Pure poison oak urushiol acetate and PDC acetate were prepared by the same method used in the preparation of the pure poison ivy urushiol acetate in Example 9. In this test thirty guinea pigs acclimatized, identified and maintained as in the preceding examples were divided into five groups of six animals each. One group was given an intravenous injection of the equivalent of 1 mg dosage unit of POU-AC and the other group was similarly injected with 10 mg equivalent dosage unit of POU-AC. Two other groups were given the equivalent of either 1 or 10 mg dosages of PDC-AC. A fifth group was given the vehicle as a control.

Two weeks after injection of the dosage units all animals were topically administered a 1 mg sensitizing dose of either PDC, HDC, or both. Attempts to sensitize the animals in each group were made with the corresponding urushiol. The control group was sensitized with 1 mg dosages of PDC-HDC mixture (1:1). Two weeks after the attempted sensitization eight sites were tested with dosages of 3, 1, and 0.3 μg each of PDC and HDC, 3 μg of PSU, and 5 μl of acetone carrier (control). All skin sites were examined for erythema and edema at 24, 48, 72 and 96 hours after application of skin test doses. Skin testing was repeated at two week intervals.

The tolerizing treatment by PDC-AC and POU-AC as in previous tests showed a rapid, profound and lasting tolerance to PDC and PSU whether or not the tolerizing dosage unit was 1 mg or 10 mg. The POU-AC single pretreatment in both 1 or 10 mg dosage units produced virtually complete tolerance to PDC and PSU throughout the tests.

EXAMPLE 12

The preceding examples clearly revealed that treatment with the acetate derivatives and red blood cell conjugates of poison ivy and poison oak urushiols produce virtually complete tolerance to poison ivy and poison sumac while producing tolerance, or a high degree of hyposensitivity to poison oak. In this test, three groups of six guinea pigs were used. The animals were acclimatized, identified and maintained as in the preceding examples. One group was sensitized topically with 1 mg PDC, the second group was sensitized with 1 mg HDC and the third group (control) was sensitized with 1 mg of a 1:1 mixture of PDC and HDC. All of the animals were skin tested with PDC and HDC two weeks following sensitization in order to obtain baseline sensitivity data before further attempts to desensitize. After the initial skin test, the group initially sensitized with PDC was given the equivalent of 10 mg of PIU-AC intravenously, the group sensitized with HDC was given an intravenous injection of 10 mg POU-AC and the control group was injected with the pharmaceutical carrier only. All animals were skin tested two weeks after treatments and at two week intervals thereafter. At the second and third skin tests after treatment (6 and 8 weeks), 3 μg of poison sumac urushiol was also used for skin testing. The procedures for sensitization, skin testing and evaluation were in accordance with the procedures described in Example 1. All solutions used in this example were prepared in the same manner as described in Example 9. All animals exhibited hypersensitivity to PDC, HDC and poison sumac. The poison ivy urushiol acetate treated group were either completely desensitized or substantially hyposensitized to subsequent skin tests with PDC for at least four weeks after treatment. Similar degree of desensitization was obtained to poison sumac. The treatment clearly revealed that the inventive compounds used to desensitize an animal to poison ivy also desensitized animals to poison sumac. Treatment with poison oak urushiol acetate conferred a rapid and complete desensitization of the test animals to both PDC and PSU. A higher degree of, and more rapid hyposensitization to poison oak urushiol was accomplished by the treatment with POU-AC than treatment with PIU-AC.

EXAMPLE 13

Thirteen naive guinea pigs, acclimatized and maintained as the animals of the previous examples were sensitized to PDC. Their respective sensitivity to 3, 1 and 0.3 μg test doses of PDC were evaluated two weeks after sensitization to obtain baseline sensitivity data. Two weeks after the initial skin tests all animals were given intravenous injections of PDC-RBC. At two and four weeks thereafter, all animals were skin tested again with 3, 1, and 0.3 μg of PDC to determine if a decrease in sensitivity (hyposensitization) had occurred. The sensitivity to PDC in all treated animals was reduced on the order of 35% to 100% in direct relation to the concentration of the test dose of PDC.

EXAMPLE 14

Forty naive guinea pigs, acclimatized, marked and maintained as in the preceding Examples were used in the test. To obtain a baseline sensitivity all animals were sensitized with PDC as in Example 12 and the sensitivity evaluated at two and four weeks thereafter. The animals were again sensitized with PDC after the four week skin test in an attempt to increase the sensitivity prior to treatment with the compounds and compositions of the invention. A third skin test was performed at seven weeks. The animals were then randomly divided into two groups. Twenty-two animals were selected for PDC-RBC treatment and eighteen were to be sham treated as controls. All of the twenty-two animals to be treated responded to the third 3 $\mu$g dosage of PDC, 68% exhibited a further hypersensitivity to the 1 $\mu$g dosage, and 32% exhibited an enhanced hypersensitivity to the 0.3 $\mu$g test dose. In the control group 88% of the animals exhibited further hypersensitivity to the third dosage of PDC in both the 3 $\mu$g and 1 $\mu$g dosages while 30% showed increased hypersensitivity to the 0.3 $\mu$g test dose.

Two weeks after the third skin test the treatment group was given a PDC-RBC dosage and the control animals were injected with sham-RBC. Each animal after treatment was given a topical application of 100 $\mu$g PDC. All animals were skin tested again two weeks after dosing with either PDC-RBC or the sham. (11th week). 25% of the animals failed to respond to the maximum 3 $\mu$g dose of PDC after treatment and the remainder of the treated animals exhibited a definite hyposensitization to these high doses of the allergen. The number of animals responding at all to 1 $\mu$g doses of PDC declined 60% and again a remarkable hyposensitization of the remaining animals was accomplished. No animals were sensitive to the 0.3 $\mu$g dosage. The substantially total loss of sensitivity to the 1 $\mu$g PDC doses coupled with the total loss of sensitivity to the 0.3 $\mu$g test dose evidenced an astounding desensitization as a result of the treatment with the PDC-RBC conjugate of the invention. The control groups did not exhibit any decrease in hypersensitivity to PDC during the tests.

EXAMPLE 15

Thirty guinea pigs were sensitized to poison ivy, poison oak and poison sumac by application to the neck skin of 0.5 mg dosages each of PDC and HDC in acetone as the carrier. Sensitizing and testing solutions and all urushiol acetate solutions were prepared as described in the preceding examples. Two weeks after sensitization with PDC and HDC all animals were skin tested with 0.01 $\mu$moles each of PDC, HDC and PSU on separate skin sites. Two weeks were allowed for the skin test sites cn the animals to heal. The animals were then randomly assigned to a first or second group of fifteen animals each. Animals in one group were given intravenous injections of an emulsion comprising 1 mg each of PIU-AC and POU-AC. The second, or control group was given the pharmaceutical carrier intravenously. At two and four weeks thereafter all animals were skin tested with 0.01 $\mu$moles of PDC, HDC and PSU. A second desensitizing dosage comprising a mixture (2 mg each) of PIU-AC and POU-AC and the carrier material was given to the respective groups after the eight week skin tests. The animals were thereafter skin tested at eleven weeks and the treated groups then administered a third dosage of 5 mg each of (PIU-POU)AC. A final skin test was given three weeks after the last desensitizing dose.

All animals were originally hypersensitive to all dosage concentrations of PDC, HDC and PSU at the first "two week" skin tests. Throughout the experiment all control animals continued to be hypersensitive to PDC, HDC and PSU. All animals treated with (PIU-POU)AC exhibited a continuing decline in sensitivity to the allergens throughout the test. After eight weeks the animals tested with HDC were also hyposensitized to that allergen.

EXAMPLE 16

The cashew nut shell extract of this example was prepared from raw cashew nuts obtained from Taiwan. The shells were carefully removed, crushed and extracted with ethanol and the ethanol extract evaporated. The residue was partitioned between chloroform and water. The chloroform extract was dried, evaporated to a definite volume and then analyzed using the same GLC procedure hereinbefore indicated. Our GC-MS analysis of the extract showed that each component of CNSO namely, anacardol, cardol and ancardic acid was actually a mixture of three olefinic congeners of each containing 1, 2, and 3 double bonds in the side chain. This indicates that CNSO is actually a mixture of nine compounds. Skin test solutions containing between 3 to 100 $\mu$g/5 $\mu$l/acetone were prepared by measuring aliquots of the analyzed chloroform solution, evaporating the solvent and dissolving the residue in acetone to give the required concentrations.

Twelve naive guinea pigs were given skin test doses of cashew nut shell oil (CNSO) ranging from 10-100 $\mu$g. Doses of 50 $\mu$g and larger caused skin irritation. A test dose of 30 $\mu$g was selected for CNSO testing because this dose elicited skin reactions on guinea pigs sensitized with poison ivy and oak and was well below the limit (50 $\mu$g) which produced skin irritation reactions.

Using the test animals of Example 15 at the fifteenth week (after the beginning of the original tests) the animals were further tested for sensitivity to CNSO. Eighty-two percent of the group receiving desensitizing injections of PIU-ac and POU-ac mixture were found to be insensitive to CNSO whereas 100% of the control animals exhibited sensitivity to CNSO. Thus treatment with PIU/POU-ac mixture produced marked desensitization to cashew nut shell liquid as well as to poison ivy and sumac.

EXAMPLES 17 AND 18

Thirty-six naive female guinea pigs acclimatized, marked and maintained as in the previous examples were used in the tests of this Example. Sensitizing solutions of PDC and HDC were prepared containing 0.5 mg each of the allergen in acetone. Skin testing solutions of PDC and of HDC contained 0.01, 0.005, and 0.002 $\mu$moles per 5 $\mu$l acetone. Because of the limited availability of skin test sites on the abdominal skin, poison sumac was tested at 0.01 $\mu$moles/5 $\mu$l acetone and cashew nut shell liquid was tested at 30 $\mu$g/5 $\mu$l acetone.

The nonadecylcatechol acetate (NDC-AC) used in the tests was prepared as follows: 2, 3 dimethoxybenzaldehyde was reduced in the presence of sodium borohydride and the reduction product reacted with phosphorus tribromide to form 2, 3 dimethoxybenzylbromide. The benzylbromide reaction product was refluxed with triphenyl phosphine in xylene to form 2, 3 dimethoxybenzyl-triphenyl phosphonium bromide which was then reacted with octadecanal in the presence of butyl lithium to form 2, 3 dimethoxy-nonadecenylbenzene. Subsequent steps of reduction and reaction with boron tribromide produced 3-nonadecylcatechol which was purified by chromatography. The catechol was acetylated with acetic anhydride in pyridine to form the acetate (NDC-AC).

The cashew nut shell extract of the example was prepared as previously mentioned in Example 16.

The animals tested were divided into three groups of twelve. Two weeks prior to attempted sensitization with the inventive compounds the animals of one group were given an intravenous injection of PIU/POU-AC solution containing an equivalent of 0.5 mg each of PIU and POU. The second group of animals were intravenously administered NDC-AC equivalent to 2 mg of NDC. The third group was used as a control and was intravenously administered the carrier material. Two weeks thereafter all animals were given topical doses of 0.5 mg PDC and 0.5 mg HDC on the neck in an attempt at sensitization. Skin tests were performed at two and five weeks after the attempted sensitization.

The results of the tests revealed that 69-92% of the animals treated with PIU/POU-AC were 100% tolerant to PDC, CNSO and PSU. A lesser degree of tolerance was observed to HDC. The NDC-AC treatment provided a limited degree of tolerance to PDC, PSU and CNSO. It was also determined and discovered during the tests that the PDC/HDC-AC mixture tolerizes the animals to all the toxic components of the cashew nut shell oil extract.

Although this invention has been described with references to illustrate embodiments thereof, it will be aparent to those skilled in the art that the principles of this invention can be embodied in other forms but within the scope of the claims.

We claim:

1. Compounds effective for tolerizing and desensitizing against contact dermatitis caused by allergens contained in plants of the Anacardiaceae and Ginkgoaceae families comprising urushiol catechols and cell membrane residues conjugaged in vitro of the formula

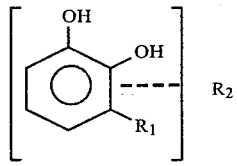

wherein $R_1$ is an alkyl radical having 11 to 19 carbon atoms, or an unsaturated congener thereof; or mixtures thereof; and $R_2$ is a cell membrane residue.

2. The compound of claim 1 wherein $R_1$ is pentadecyl and the cell membrane residues are cell membrane residues of autologous red blood cells.

3. The compound of claim 1 wherein $R_1$ is heptadecyl and the cell membrane residues are cell membrane residues of autologous red blood cells.

4. The compound of claim 1 wherein $R_1$ is nonadecyl and the cell membrane residues are cell membrane residues of autologous red blood cells.

5. The compound of claim 1 wherein $R_1$ is mono-olefinic pentadecyl and the cell membrane residues are cell membrane residues of autologous red blood cells.

6. The compound of claim 1 wherein $R_1$ is mono-olefinic heptadecyl and the cell membrane residues are cell membrane residues of autologous red blood cells.

7. The compound of claim 1 wherein $R_1$ is diolefinic pentadecyl and the cell membrane residues are cell membrane residues of autologous red blood cells.

8. The compound of claim 1 wherein $R_1$ is diolefinic heptadecyl and the cell membrane residues are cell membrane residues of autologous red blood cells.

9. The compound of claim 1 wherein $R_1$ is triolefinic pentadecyl and the cell membrane residues are cell membrane residues of autologous red blood cells.

10. The compound of claim 1 wherein $R_1$ is triolefinic heptadecyl and the cell membrane residues are cell membrane residues of autologous red blood cells.

11. The compounds of claim 1 wherein the cell membrane residues are cell membrane residues selected from the group consisting of autologous red blood cells, lymph cells, white blood cells, spleen cells and lympth node cells.

12. Compositions useful for tolerizing and desensitization of mammals against allergens contained in plants of the Anacardiaceae and Ginkgoaceae families consisting essentially of a compound having the formula:

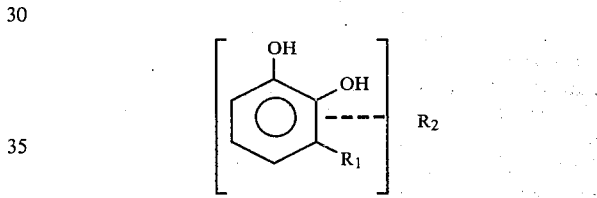

wherein $R_1$ is an alkyl radical having 11–19 carbon atoms and the unsaturated congeners thereof and mixtures thereof; and $R_2$ is selected from the group consisting of an acylester functioning group hydrolyzable in vivo esterifying the catecholic hydroxy groups, and cell membrane residues in admixture with a non-toxic pharmaceutically acceptable carrier in a therapeutically effective concentration.

13. The composition of claim 12 wherein $R_1$ of said composition is pentadecyl and $R_2$ is cell membrane residues of autologous red blood cells.

14. The composition of claim 12 wherein $R_1$ of said compound is pentadecyl and $R_2$ is acetate.

15. The composition of claim 12 wherein $R_1$ of said compound is heptadecyl and $R_2$ is cell membrane residues of autologous red blood cells.

16. The composition of claim 12 wherein $R_1$ of said compound is heptadecyl and $R_2$ is acetate.

17. The composition of claim 12 wherein $R_1$ of said compound is nonadecyl and $R_2$ is acetate.

18. The composition of claim 12 wherein $R_1$ of said compound is nonadecyl and $R_2$ is cell membrane residues of autologous red blood cells.

19. The composition of claim 12 wherein $R_1$ of said compound is mono-olefinic pentadecyl and $R_2$ is cell membrane residues of autologous red blood cells.

20. The composition of claim 12 wherein $R_1$ of said compound is mono-olefinic heptadecyl and $R_2$ is cell membrane residues of autologous red blood cells.

21. The composition of claim 12 wherein $R_1$ of said compound is mono-olefinic pentadecyl and $R_2$ is acetate.

22. The composition of claim 12 wherein $R_1$ of said compound is mono-olefinic heptadecyl and $R_2$ is acetate.

23. The composition of claim 12 wherein $R_1$ of said compound is diolefinic pentadecyl and $R_2$ is cell membrane residues of autologous red blood cells.

24. The composition of claim 12 wherein $R_1$ of said compound is diolefinic heptadecyl and $R_2$ is cell membrane residues of autologous red blood cells.

25. The composition of claim 12 wherein $R_1$ of said compound is diolefinic pentadecyl and $R_2$ is acetate.

26. The composition of claim 12 wherein $R_1$ of said compound is diolefinic heptadecyl and $R_2$ is acetate.

27. The composition of claim 12 wherein $R_1$ of said compound is triolefinic pentadecyl and $R_2$ is cell membrane residues of autologous red blood cells.

28. The composition of claim 12 wherein $R_1$ of said compound is triolefinic heptadecyl and $R_2$ is cell membrane residues of autologous red blood cells.

29. The composition of claim 12 wherein $R_1$ of said compound is triolefinic pentadecyl and $R_2$ is acetate.

30. The composition of claim 12 wherein $R_1$ of said compound is triolefinic heptadecyl and $R_2$ is acetate.

31. The composition of claim 12 wherein said mixture of compounds is a mixture of one or more of pentadecylcatechol and the unsaturated congeners thereof conjugated with the cell membrane residues of autologous red blood cells.

32. The composition of claim 12 wherein said mixture of compounds consists essentially of a mixture of one or more of heptadecylcatechol acetates and the unsaturated congeners thereof.

33. The composition of claim 12 wherein said mixture of compounds is a mixture of one or more of heptadecylcatechol and the unsaturated congeners thereof conjugated with the cell membrane residues of autologous red blood cells.

34. The composition of claim 12 wherein said mixture of compounds is a mixture of acetates of pentadecylcatechol and the unsaturated congeners thereof.

35. Compositions effective for tolerizing and desensitization of mammals against contact dermatitis caused by allergens contained in plants of the Anacardiaceae and Ginkgoaceae families comprising the reaction products of a first material selected from the group consisting of poison ivy urushiol, poison oak urushiol, poison sumac urushiol, and mixtures thereof; and a second material selected from an acyl ester functioning compound hydrolyzable in vivo and cell membrane residues in admixture with a non-toxic pharmaceutically acceptable carrier in a therapeutically effective concentration.

36. The composition of claim 35 wherein said first material is poison ivy urushiol and said second material is the cell membrane residue of autologous red blood cells.

37. The composition of claim 35 wherein said first material is poison oak urushiol and said second material is the cell membrane residue of autologous red blood cells.

38. The composition of claim 35 wherein said first material is a mixture of poison oak urushiol and poison ivy urushiol and said second material is the cell membrane residue of autologous red blood cells.

39. The composition of claim 35 wherein said first material is poison sumac urushiol and said second material is the cell membrane residue of autologous red blood cells.

40. The composition of claim 35 wherein said first material is poison ivy urushiol and said second material is acetic anhydride.

41. The composition of claim 35 wherein said first material is poison oak urushiol and said second material is acetic anhydride.

42. The composition of claim 35 wherein said first material is a mixture of poison oak urushiol and poison ivy urushiol and said second material is acetic anhydride.

43. The composition of claim 35 wherein said first material is poison sumac urushiol and said second material is acetic anhydride.

44. The method of tolerizing and desensitizing mammals to allergens contained in plants of the Anacardiaceae and Ginkgoaceae families which consists essentially of administering to said mammal a composition consisting essentially of a compound or mixture of compounds having the formula:

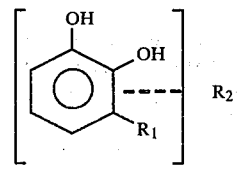

wherein $R_1$ is an alkyl radical having 11 to 19 carbon atoms and the unsaturated congeners thereof and mixtures thereof; and $R_2$ is selected from the group consisting of an acyl ester functioning group hydrolyzable in vivo esterifying the catecholic hydroxy group and cell membrane residues in admixture with a non-toxic pharmaceutically acceptable carrier, said compound or mixture of compounds being in a therapeutically effective concentration.

45. The method of claim 44 wherein said compound is pentadecylcatechol conjugated to the cell membrane residue of autologous red blood cells.

46. The method of claim 44 wherein said compound is pentadecylcatechol acetate.

47. The method of claim 44 wherein said compound is heptadecylcatechol conjugated to the cell membrane residue of autologous red blood cells.

48. The method of claim 44 wherein said compound is heptadecylcatechol acetate.

49. The method of claim 44 wherein said compound is a mixture of heptadecylcatechol acetate and pentadecylcatechol acetate.

50. The method of claim 44 wherein said compound is a mixture of heptadecylcatechol and pentadecylcatechol conjugated to the cell membrane residue of autologous red blood cells.

51. The method of claim 44 wherein said compound is nonadecylcatecholacetate.

52. The method of claim 44 wherein said compound is nonadecylcatechol conjugated to the cell membrane residue of autologous red blood cells.

53. The method of claim 44 wherein $R_1$ of said compound is mono-olefinic pentadecylcatechol and $R_2$ is cell membrane residues of autologous red blood cells.

54. The method of claim 44 wherein $R_1$ of said compound is mono-olefinic heptadecylcatechol and $R_2$ is cell membrane residues of autologous red blood cells.

55. The method of claim 44 wherein said compound is a monoolefinic pentadecylcatechol acetate.

56. The method of claim 44 wherein said compound is a monoolefinic heptadecylcatechol acetate.

57. The method of claim 44 wherein $R_1$ of said compound is diolefinic pentadecylcatechol and $R_2$ is cell membrane residues of autologous red blood cells.

58. The method of claim 44 wherein $R_1$ of said compound is diolefinic heptadecylcatechol and $R_2$ is cell membrane residues of autologous red blood cells.

59. The method of claim 44 wherein said compound is a diolefinic pentadecylcatechol acetate.

60. The method of claim 44 wherein said compound is a diolefinic heptadecylcatechol acetate.

61. The method of claim 44 wherein $R_1$ of said compound is triolefinic pentadecylcatechol and $R_2$ is cell membrane residues of autologous red blood cells.

62. The method of claim 44 wherein $R_1$ of said compound is triolefinic heptadecylcatechol and $R_2$ is cell membrane residues of autologous red blood cells.

63. The method of claim 44 wherein said compound is a triolefinic pentadecylcatechol acetate.

64. The method of claim 44 wherein said compound is a triolefinic heptadecylcatechol acetate.

65. The method of claim 44 wherein said mixture of compounds consists essentially of a mixture of one or more of pentadecylcatechol and the unsaturated congeners thereof conjugated with the cell membrane residues of autologous red blood cells.

66. The method of claim 44 wherein said mixture of compounds consists essentially of a mixture of one or more of heptadecylcatechol acetate and the unsaturated congeners thereof.

67. The method of claim 33 wherein said mixture of compounds consists essentially of a mixture of one or more of the acetates of pentadecylcatechol and the unsaturated congeners thereof.

68. The method of claim 33 wherein said mixture of compounds consists essentially of a mixture of one or more of heptadecylcatechol and the unsaturated congeners thereof conjugated with the cell membrane residues of autologous red blood cells.

* * * * *